United States Patent
Wawrzyniak

(10) Patent No.: US 12,329,408 B2
(45) Date of Patent: Jun. 17, 2025

(54) HANDLE DESIGN OF A SCALPEL FOR STABLE OPERATION THEREOF

(71) Applicant: Michael Joseph Wawrzyniak, Las vegas, NV (US)

(72) Inventor: Michael Joseph Wawrzyniak, Las vegas, NV (US)

( * ) Notice: Subject to any disclaimer, the term of this patent is extended or adjusted under 35 U.S.C. 154(b) by 456 days.

(21) Appl. No.: 17/377,407

(22) Filed: Jul. 16, 2021

(65) Prior Publication Data

US 2023/0015568 A1 Jan. 19, 2023

(51) Int. Cl.
| | | |
|---|---|---|
| *A61B 17/3213* | (2006.01) | |
| *B25G 1/10* | (2006.01) | |
| *B25G 3/08* | (2006.01) | |
| *A61B 17/00* | (2006.01) | |

(52) U.S. Cl.
CPC .......... *A61B 17/3213* (2013.01); *B25G 1/102* (2013.01); *B25G 3/08* (2013.01); *A61B 2017/00424* (2013.01); *A61B 2017/00429* (2013.01); *A61B 2017/00477* (2013.01)

(58) Field of Classification Search
CPC ...... A61B 17/3213; A61B 2017/00477; A61B 2017/00424; A61B 2017/00429; B25G 1/02; B25G 3/08; B25G 3/00
USPC .......................................................... 30/337
See application file for complete search history.

(56) References Cited

U.S. PATENT DOCUMENTS

| | | | |
|---|---|---|---|
| 2,215,125 A | 9/1940 | Maxwell | |
| 2,257,141 A | 9/1941 | Waugh | |
| 3,262,205 A * | 7/1966 | Arden | A61B 17/3213 D24/147 |
| 3,373,491 A | 3/1968 | Montelius | |
| 3,748,736 A | 7/1973 | Eisen | |
| 5,299,357 A | 4/1994 | Wonderley et al. | |
| 5,309,641 A | 5/1994 | Wonderley et al. | |

(Continued)

FOREIGN PATENT DOCUMENTS

| | | |
|---|---|---|
| CN | 201595905 U | 10/2010 |
| CN | 107811681 A | 3/2018 |

(Continued)

OTHER PUBLICATIONS

Translation of KR 101538917 B1 (Year: 2024).*

(Continued)

*Primary Examiner* — Nhat Chieu Q Do
(74) *Attorney, Agent, or Firm* — LEGALFORCE RAPC WORLDWIDE

(57) ABSTRACT

A scalpel handle includes a receiving member to receive a blade therethrough and a main portion coupled to the receiving member. The main portion has a number of indentations on both a first surface and a second surface thereof. The indentations are evenly spaced between one another and the number of indentations extends from a first end proximate the receiving member along a first length of the main portion across an entire width thereof. The first length is at least two-thirds of a second length of an entirety of the main portion. The width of the main portion is at least five times a maximum width of the receiving member. A thickness of the main portion is at least 2.5 times a maximum thickness of the receiving member. All outer surfaces of the main portion including the first surface and the second surface are convex in shape around edges thereof.

18 Claims, 7 Drawing Sheets

(56) References Cited

U.S. PATENT DOCUMENTS

| | | |
|---|---|---|
| 5,312,429 A | 5/1994 | Noack |
| 5,527,329 A | 6/1996 | Gharibian |
| 5,571,127 A | 11/1996 | DeCampli |
| 5,868,771 A * | 2/1999 | Herbert .............. A61B 17/3213 30/162 |
| 5,938,676 A | 8/1999 | Cohn et al. |
| 6,569,175 B1 | 5/2003 | Robinson |
| 7,022,128 B2 | 4/2006 | Morawski et al. |
| 7,153,317 B2 | 12/2006 | Kanodia et al. |
| 7,201,760 B2 | 4/2007 | Masury et al. |
| 7,314,471 B2 | 1/2008 | Holman |
| 7,527,635 B2 | 5/2009 | Saito et al. |
| 7,669,337 B2 | 3/2010 | Yi et al. |
| 8,256,330 B2 | 9/2012 | Auchter et al. |
| 8,282,662 B2 | 10/2012 | Reaux |
| 8,291,601 B2 | 10/2012 | Kehr et al. |
| 8,409,231 B2 | 4/2013 | Dunn |
| 8,567,072 B2 | 10/2013 | Yi et al. |
| 8,814,893 B2 | 8/2014 | Cote et al. |
| 8,819,943 B2 | 9/2014 | Maxwell |
| 8,850,662 B2 | 10/2014 | Gitman et al. |
| 8,898,910 B2 | 12/2014 | Ichiyanagi et al. |
| 8,959,778 B2 | 2/2015 | Baid |
| 9,757,146 B2 | 9/2017 | Vodinh |
| 10,092,314 B2 | 10/2018 | Castanon et al. |
| D857,886 S | 8/2019 | Zepf |
| 10,478,218 B2 | 11/2019 | Wendenburg |
| 11,000,309 B2 | 5/2021 | Milton et al. |
| 2003/0200665 A1 | 10/2003 | Li |
| 2006/0041266 A1 | 2/2006 | Sullivan et al. |
| 2009/0192538 A1 | 7/2009 | Sandel et al. |
| 2009/0204137 A1 | 8/2009 | Maxwell |
| 2010/0005630 A1* | 1/2010 | Gitman ................. B25G 1/102 606/167 |
| 2010/0268258 A1 | 10/2010 | Maxwell |
| 2013/0245655 A1 | 9/2013 | Mahurkar |
| 2014/0059863 A1 | 3/2014 | Ichiyanagi et al. |
| 2015/0119913 A1 | 4/2015 | Kanigan |
| 2015/0164539 A1* | 6/2015 | Kanigan ............ A61B 17/3213 606/167 |
| 2015/0257777 A1* | 9/2015 | Woodward ......... A61B 17/3211 606/167 |
| 2018/0303510 A1* | 10/2018 | Levy ................. A61B 17/3213 |
| 2019/0274667 A1* | 9/2019 | Freshly ................. B25G 1/102 |
| 2019/0275660 A1* | 9/2019 | Mann ................. A61B 17/3213 |
| 2020/0121348 A1 | 4/2020 | Milton et al. |
| 2020/0163690 A1 | 5/2020 | Austria et al. |
| 2022/0096114 A1* | 3/2022 | Spiro ................... B24B 37/042 |

FOREIGN PATENT DOCUMENTS

| | | |
|---|---|---|
| CN | 212165858 U * | 12/2020 |
| KR | 20130136842 A * | 12/2013 |
| KR | 101538917 B1 * | 7/2015 |
| WO | 2010132027 A2 | 11/2010 |
| WO | WO-2020112755 A1 * | 6/2020 ......... A61B 17/3211 |

OTHER PUBLICATIONS

Translation CN 212165858 (Year: 2024).*
Translation KR20130136842 (Year: 2024).*
"Scalpel Handle" by Scalpel Innovation, Found Online on [Aug. 9, 2021] https://vimeo.com/135527894.
"Scalpel Handle, Stainless Steel, #3L—AJ142" by MOPEC, Found Online on [Aug. 9, 2021] https://www.mopec.com/product/scalpel-handle-stainless-steel-3l-aj142/.
"Scalpel Handle Flat No. 3" by GDC Dental, Found Online on [Aug. 9, 2021] https://www.gdcdental.com/product-scalpel-handle-flat-no-3-266.php.
"Scalpel Handle No. 3 (125 mm)" by WITTEX, Found Online on [Aug. 9, 2021] https://mimera.com/en/scalpel-handle-no-3-wittex.
"Ergonomic handle scalpel 8001307" by Keystone Vet, Found Online on [Aug. 9, 2021] https://www.medicalexpo.com/prod/keystone-vet/product-119253-826162.html.

* cited by examiner

HANDLE DESIGN OF A SCALPEL FOR STABLE OPERATION THEREOF

FIELD OF TECHNOLOGY

This disclosure relates generally to medical/surgical appliances and, particularly, to a device, a system and/or a method of a handle design of a scalpel for stable operation thereof.

BACKGROUND

A scalpel may be used in applications including but not limited to arts and crafts, dissection and surgery. The scalpel may include a handle and a blade received therein. The handle may have indentations thereon and may have a thickness comparable to the thickness of the blade. During use of the scalpel, the user may find that the scalpel slips from a hand thereof.

SUMMARY

Disclosed are a device, a system and/or a method of a handle design of a scalpel for stable operation thereof.

In one aspect, a scalpel handle includes a receiving member to receive a blade therethrough and a main portion coupled to the receiving member. The main portion has a number of indentations on both a first surface and a second surface thereof. The indentations are evenly spaced between one another and the number of indentations extends from a first end proximate the receiving member along a first length of the main portion across an entire width thereof. The first length is at least two-thirds of a second length of an entirety of the main portion. The width of the main portion is at least five times a maximum width of the receiving member. A thickness of the main portion is at least 2.5 times a maximum thickness of the receiving member. All outer surfaces of the main portion including the first surface and the second surface are convex in shape around edges thereof.

In another aspect, a scalpel includes a blade and a handle. The handle includes a receiving member receiving the blade therethrough and a main portion coupled to the receiving member. The main portion has a number of indentations on both a first surface and a second surface thereof. The indentations of the number of indentations are evenly spaced between one another and the number of indentations extends from a first end proximate the receiving member along a first length of the main portion across an entire width thereof. The first length is at least two-thirds of a second length of an entirety of the main portion. The width of the main portion is at least five times a maximum width of the receiving member. A thickness of the main portion is at least 2.5 times a maximum thickness of the receiving member. All outer surfaces of the main portion including the first surface and the second surface are convex in shape around edges thereof.

In yet another aspect, a scalpel handle includes a receiving member to receive a blade therethrough and a main portion coupled to the receiving member. The main portion has a number of indentations on both a first surface and a second surface thereof. The indentations of the number of indentations are evenly spaced between one another and the number of indentations extends from a first end proximate the receiving member along a first length of the main portion across an entire width thereof. The first length is at least two-thirds of a second length of an entirety of the main portion. The width of the main portion is at least five times a maximum width of the receiving member. A thickness of the main portion is at least 2.5 times a maximum thickness of the receiving member. All outer surfaces of the main portion including the first surface and the second surface are convex in shape around edges thereof. The width of the main portion tapers from a second end thereof farthest away from the receiving member to a third end thereof closest to the receiving member, with the third end being proximate the first end and the width of the main portion at the third end still being at least five times the maximum width of the receiving member.

The methods and systems disclosed herein may be implemented in any means for achieving various aspects. Other features will be apparent from the accompanying drawings and from the detailed description that follows.

BRIEF DESCRIPTION OF THE DRAWINGS

Example embodiments are illustrated by way of example and not limitation in the figures of accompanying drawings, in which like references indicate similar elements and in which.

Other features of the present embodiments will be apparent from the accompanying drawings and from the detailed description that follows.

DETAILED DESCRIPTION

Example embodiments, as described below, may be used to realize a handle design of a scalpel for stable operation thereof. It will be appreciated that the various embodiments discussed herein need not necessarily belong to the same group of exemplary embodiments, and may be grouped into various other embodiments not explicitly disclosed herein. In the following description, for purposes of explanation, numerous specific details are set forth in order to provide a thorough understanding of the various embodiments.

Figure 1:
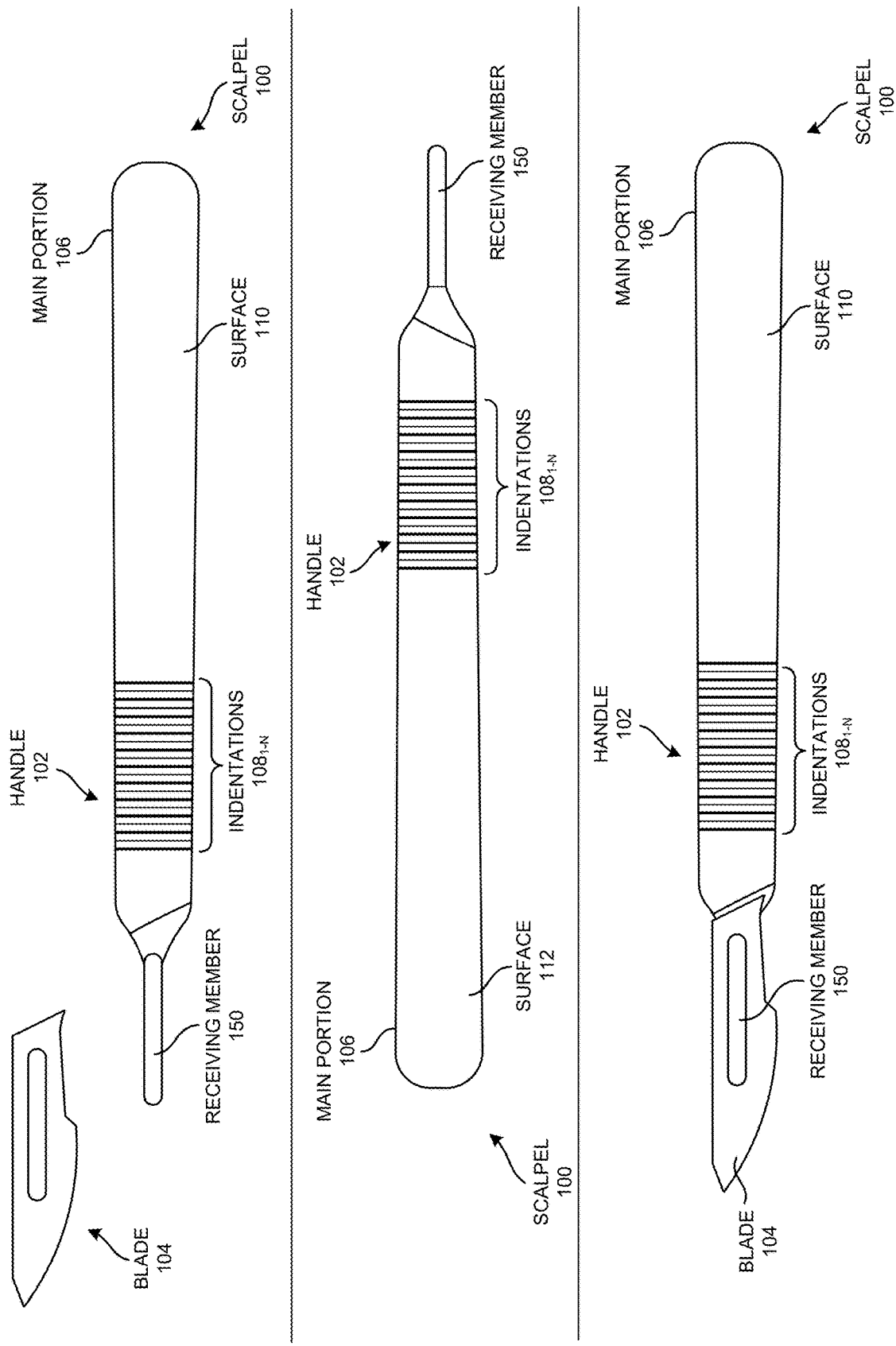
FIG. 1 is a front view of a scalpel in a traditional implementation thereof.

FIG. 1 shows a scalpel 100 in accordance with a traditional implementation. Scalpel 100, as discussed herein, may used in a lot of applications including but not limited to arts and crafts, dissection and surgery. Scalpel 100 may include a handle 102 and a blade 104. Blade 104 may be replaceable such that handle 102 may be reused with a replacement blade 104. Blade 104 may, for example, be made of stainless steel and handle 102 may be made of plastic or stainless steel. While a length of blade 104 may typically be lesser than a length of a main portion 106 of handle 102, main portion 106 may have a number of indentations $108_{1-N}$ on each of a surface 110 and a surface 112 of main portion 106 along a length thereof; these indentations $108_{1-N}$ may evenly spaced between one another such that a length of an entirety of the number of indentations $108_{1-N}$ may be much less than half the length of main portion 106. Main portion 106 of handle 102 may be understood as handle 102 excluding a receiving member 150 thereof. Receiving member 150 of handle 102 may enable reception of blade 104 therewithin.

Figure 2:
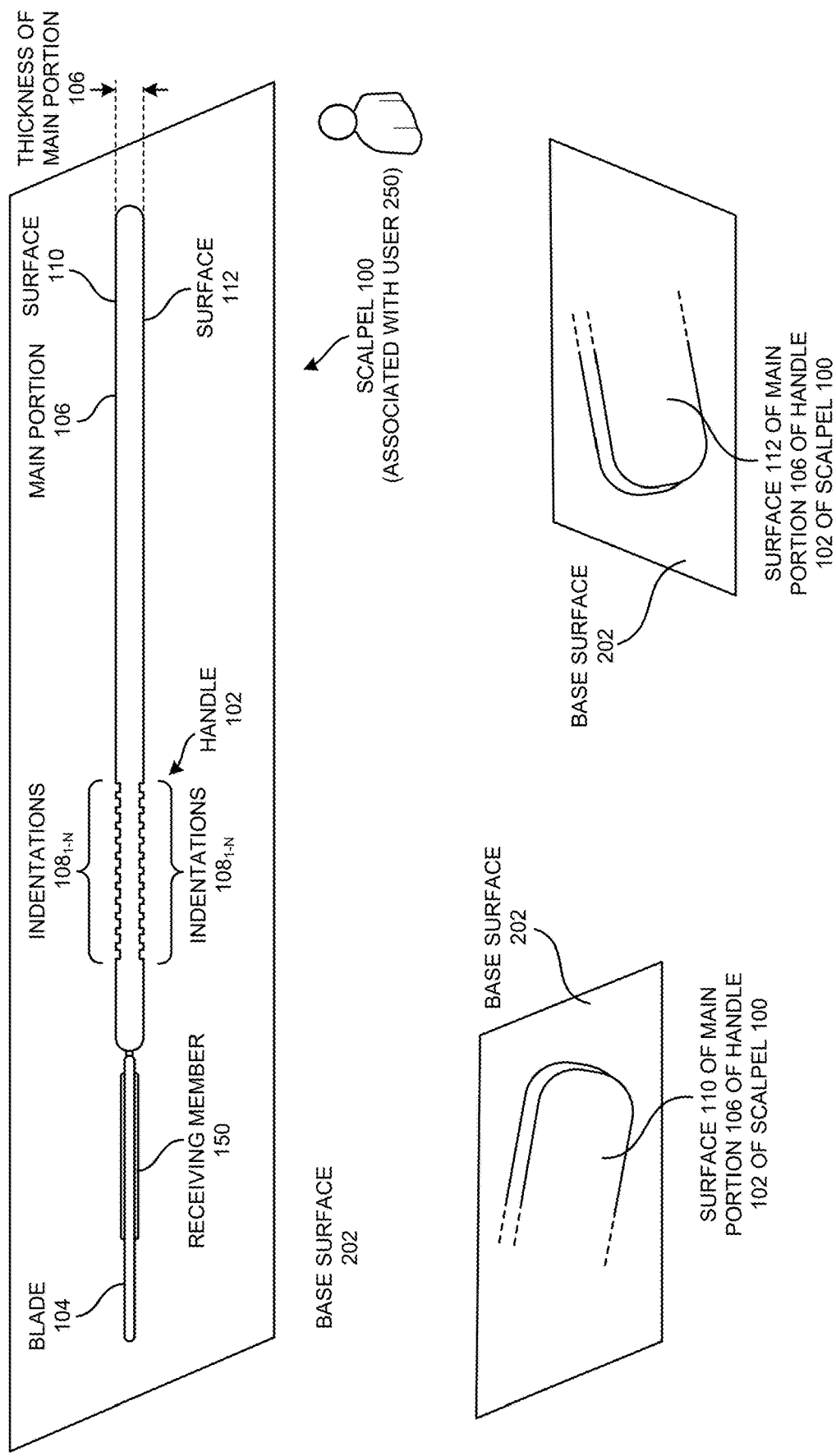
FIG. 2 is a top view of the scalpel of FIG. 1.
Figure 3:
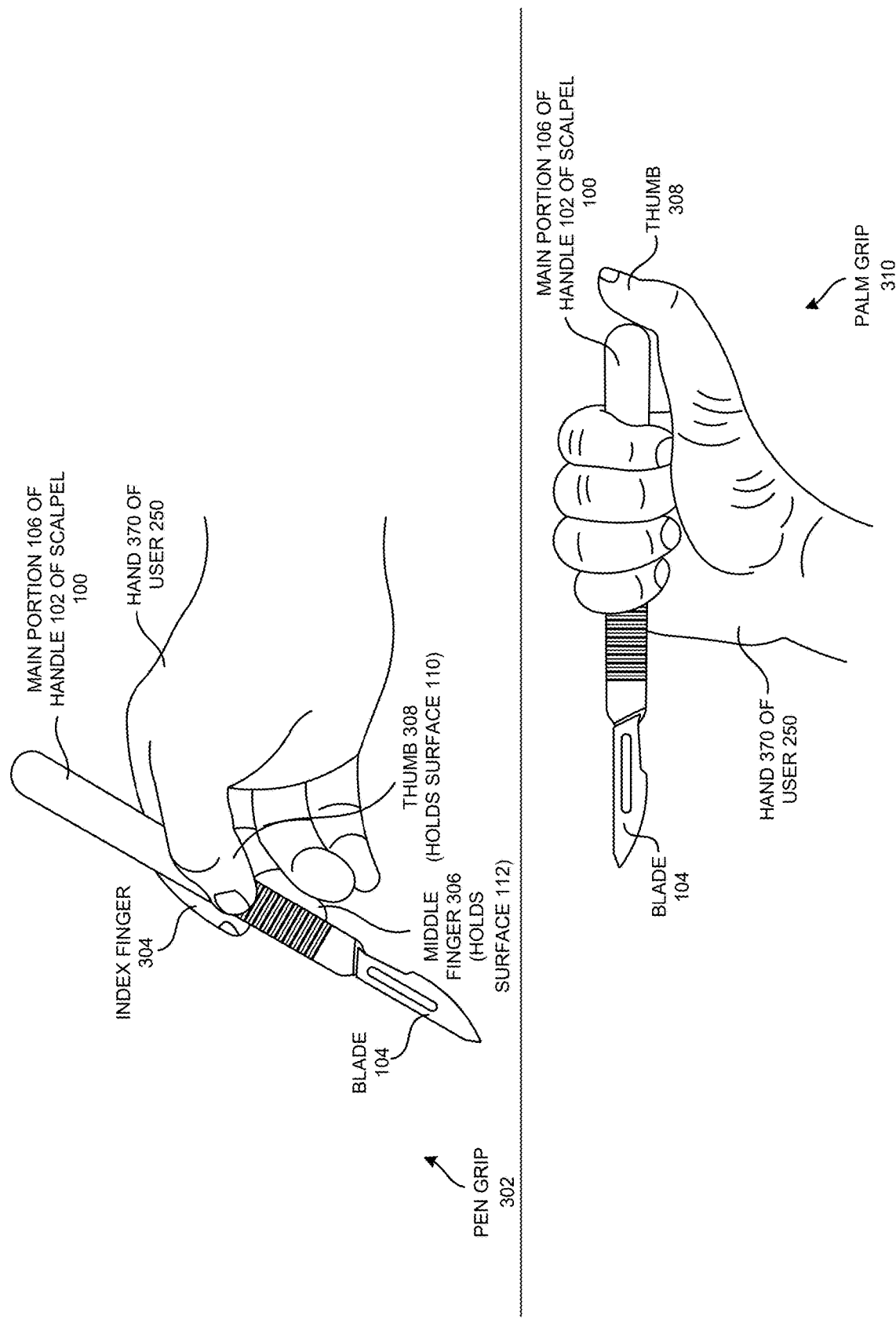
FIG. 3 is an illustrative view of a pen grip hold and a palm grip hold of the scalpel of FIG. 1 by a user thereof.

FIG. 2 shows a top view of scalpel 100. Here, scalpel 100 may be placed on a base surface 202 by way of sharp edges thereof such that surface 110 and surface 112 may be perpendicular to base surface 202. As seen in FIG. 2, a thickness of main portion 106 corresponding to a shortest distance between a non-indented portion of surface 110 and a non-indented portion of surface 112 may be comparable to a thickness of blade 104. This may render edges of main portion 106 sharp such that a user 250 rotating main portion 106 of handle 102 of scalpel 100 in a hand thereof during use of scalpel 100 may find said edges providing too small an area for stable movement of main portion 106, thereby making it difficult to handle scalpel 100. FIG. 3 shows a pen grip 302 hold by user 250 of scalpel 100, where an index finger 304 of a hand 370 of user 250 rests on top of the thickness of main portion 106 and a middle finger 306 and a thumb 308 of hand 370 of user 250 hold main portion 106 on surface 112 and surface 110 respectively.

FIG. 3 also shows a palm grip 310 hold by user 250 of scalpel 100 when a task to be accomplished through scalpel 100 requires more strength on part of user 250. Here, user 250 may hold main portion 106 in a palm of hand 370 thereof with all fingers thereof except thumb 308 closed over main portion 106; thumb 308 may rest on an outer edge of main portion 106 that offers very less surface area. The difficulties associated with rotation of main portion 106 of handle 102/scalpel 100 within hand 370 of user 250 may not be the only ones posed; the length of main portion 106, the small length of the number of indentations $108_{1-N}$ thereon and the small surface area of the edges due to sharpness thereof may apply a lot of pressure on the fingers of hand 370 of user 250.

Thus, in the typical implementation of scalpel 100, not only may the length of main portion 106 serve as an inconvenience to a user 250 with long fingers and a long hand 370 to whom a longer main portion 106 would be preferable but also the small length of the number of indentations $108_{1-N}$, the sharp edges of main portion 106 and the small thickness of main portion 106 may serve to manifest instability of scalpel 100 with respect to performing tasks associated therewith. When user 250 has a large hand 370 and long fingers, the small length of the number of indentations $108_{1-N}$, the short length of main portion 106, the sharp edges of main portion 106 and/or the small thickness of main portion 106 may serve to frustrate user 250 during use of scalpel 100 and/or may cause slippage thereof.

Figure 4:
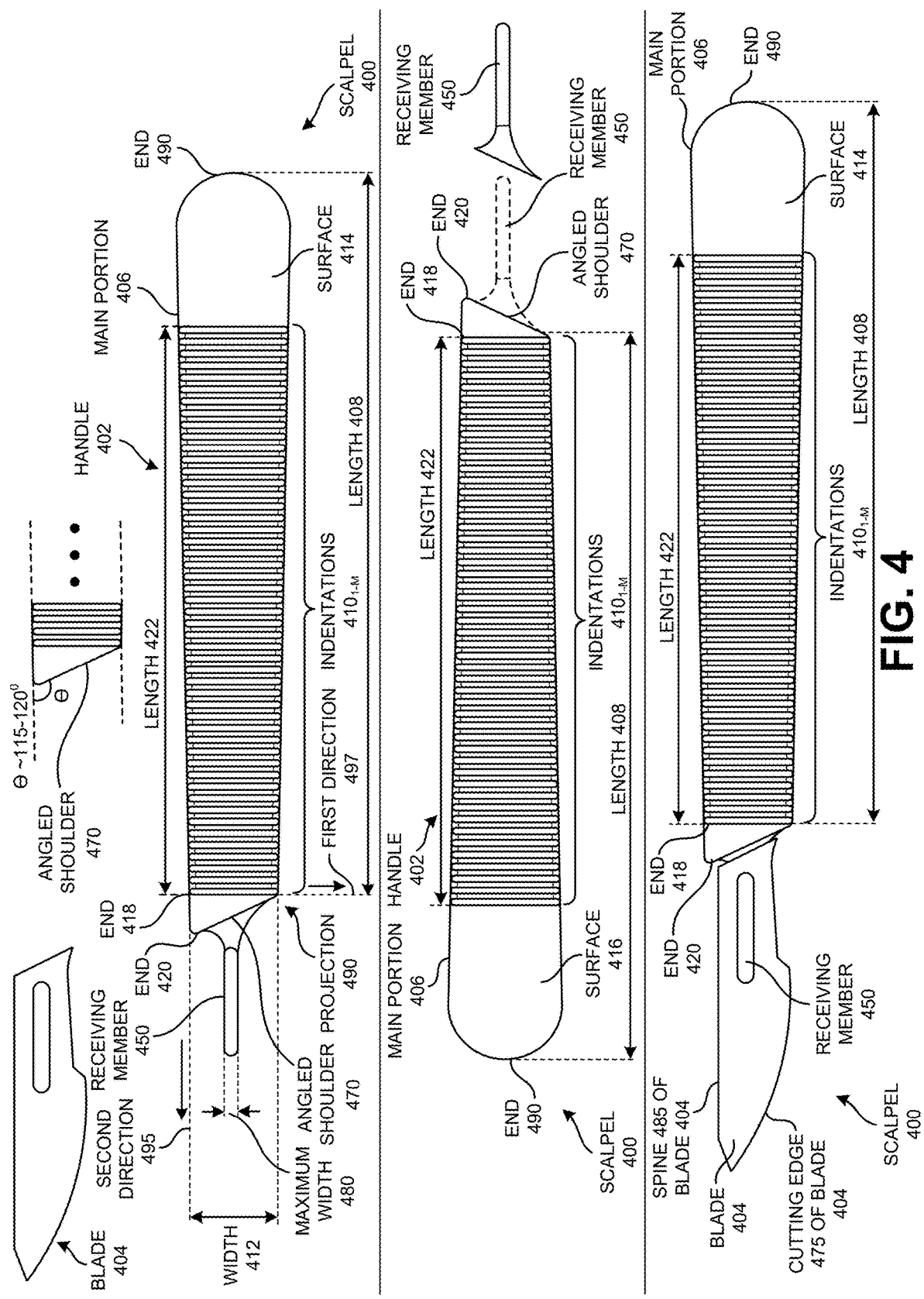
FIG. 4 is a front view of a scalpel, according to one or more embodiments.

FIG. 4 shows a scalpel 400 that serves to solve problems associated with scalpel 100, according to one or more embodiments. Although exemplary embodiments may preferentially be employed in medical/surgical applications, other uses are within the scope of the exemplary embodiments discussed herein. As seen above, in one or more embodiments, scalpel 400 may include a handle 402 receiving a blade 404 therewithin. In one or more embodiments, blade 404 may be removable from handle 402 and replaceable, and handle 402 may be reusable. Again, in one or more embodiments, handle 402 may be made of stainless steel or plastic and blade 404 may be made of stainless steel. Other materials are within the scope of the exemplary embodiments discussed herein.

In one or more embodiments, handle 402 may include a main portion 406 that is handle 402 excluding a blade receiving member (to be discussed). In one or more embodiments, main portion 406 may be the portion of handle 402 that user 250 contacts with hand 370 during use of scalpel 400. In one or more embodiments, a length 408 of main portion 406 may have a number of indentations $410_{1-M}$, each of which extends across an entire width 412 of main portion 406. Again, in one or more embodiments, indentations $410_{1-M}$ may be provided on each surface (414, 416) of main portion 406 along length 408. In one or more embodiments, indentations $410_{1-M}$ may be evenly spaced between one another such that the number of indentations $410_{1-M}$ may extend from an end 418 of main portion 406 proximate an end 420 closest to blade 404 (or receiving member thereof) to a length 422 that is at least two-thirds of length 408 of main portion 406.

In one or more embodiments, handle 402 may include a receiving member 450 to receive blade 404 therewithin. In some embodiments, receiving member 450 may be removably coupled (e.g., connected) to main portion 406 and, in some other embodiments, receiving member 450 may be an extension of main portion 406. FIG. 4 also shows an angled shoulder 470 of main portion 406 at end 420 closest to blade 404 (or receiving member 450) in a state of reception thereof. In one example embodiment, the angle made by angled shoulder 470 with respect to a length of handle 402 may be approximately 115-120°. In one or more embodiments, a maximum width 480 of receiving member 450 may be at least five times less than width 412 of main portion 406. In some embodiments, width 412 of main portion 406 may be varying and may be smallest at end 420 closest to blade 404 (or receiving member 450) and longest at an end 490 farthest from blade 404 (or receiving member 450) in the state of reception thereof. Main portion 406 with equal width 412 across an entire length 408 thereof may also be within the scope of the exemplary embodiments discussed herein.

Figure 5:
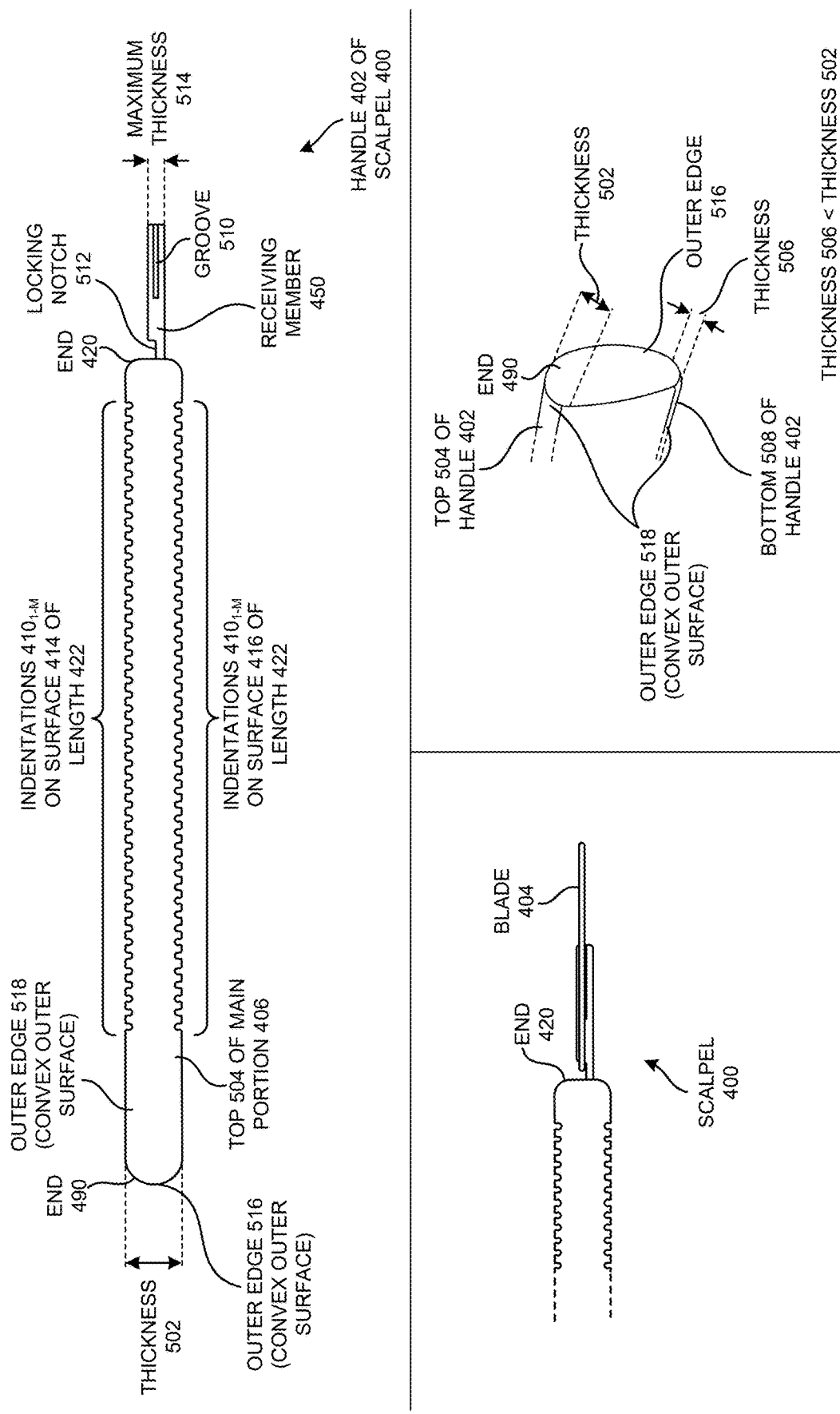
FIG. 5 is a top view of the scalpel of FIG. 4, according to one or more embodiments.

In other words, width 412 of main portion 406 may taper from end 490 to end 420. In one or more embodiments, the smallest width 412 of main portion 406 at end 420 closest to blade 404 (or receiving member 450) may still be at least five times more than a maximum width (e.g., width 480) of receiving member 450. FIG. 5 shows a top view of scalpel 400, according to one or more embodiments. In one or more embodiments, including outer edges of indentations $410_{1-M}$, a thickness 502 of main portion 406 at a top 504 thereof may be more than a thickness 506 of main portion 406 at a bottom 508 thereof. In one or more embodiments, thickness 502 and thickness 506 may be along a dimension perpendicular to both length 408 and width 412. In one or more embodiments, thickness 502 at top 504 may provide a surface to rest index finger 304 of hand 370 of user 250 during use of scalpel 400.

As seen in FIG. 5, receiving member 450 may have a groove 510 along a length thereof through which blade 404 is slid, according to one or more embodiments. In one or more embodiments, receiving member 450 may also have a locking notch 512 proximate end 420 to enable receiving member 450 wrap around and lock onto blade 404. FIG. 5 shows scalpel 400 with blade 404 connected thereto, according to one or more embodiments. In one or more embodiments, a maximum thickness 514 of receiving member 450 may be at least 2.5 times less than thickness 502/506 of main portion 406.

Further, as seen in FIG. 5, outer edges (516, 518) of main portion 406 at end 490 and on top 504 (thickness 502) and bottom 508 (thickness 506) thereof may be convex without sharp edges, according to one or more embodiments. In other words, in one or more embodiments, all outer surfaces of main portion 406 including surface 414 and surface 416 are convex in shape around edges (e.g., outer edge 516, outer edge 518) thereof. In one or more embodiments, this, in conjunction with flat surfaces provided along length 408 and width 412 of main portion 406, may provide for less pressure applied to fingers of hand 370 of user 250 during performance of tasks using scalpel 400. Further, in one or more embodiments, the anti-slippage characteristics of indentations 410$_{1-M}$ may enable user 250 to have a good grip of main portion 406. In one or more embodiments, as the total length 422 of these evenly spaced indentations 410$_{1-M}$ is higher than the corresponding length in scalpel 100, a user 250 with a longer hand 370/fingers thereof may find it easier to hold main portion 406 and rotate main portion 406 within hand 370 during the course of performing tasks with scalpel 400.

In one or more embodiments, handle 402 may be manufactured with longer main portion 406 such that length 422 may appropriately scale with length 408. As seen above, in one or more embodiments, length 422 may be at least two-thirds of length 408. In one or more embodiments, longer length 408 and, therefore, longer length 422 may enable user 250 to grip main portion 406 across a longer distance without slippage.

In one example implementation, length 408 of main portion 406 may be ~110-120 mm and length 422 of the number of indentations 410$_{1-M}$ may be ~82-85 mm; thus, length 422 may be more than two-thirds of length 408. Here, width 412 of main portion 406 may vary from ~19-20 mm at end 490 and ~13-14 mm at end 420, and (maximum) width 480 of receiving member 450 may be ~2.3-2.5 mm; thus, width 412 may always be at least five times more than (maximum) width 480 of receiving member 450. Also, thickness 502 may be ~8.5-8.6 mm and thickness 506 may be ~6.9-7 mm, and maximum thickness 514 of receiving member 450 may be ~2.5-2.6 mm; thus, thickness (502, 506) may be at least 2.5 times maximum thickness 514 of receiving member 450. Other numbers based on the aforementioned ratios are also within the scope of the exemplary embodiments discussed herein.

Figure 6:
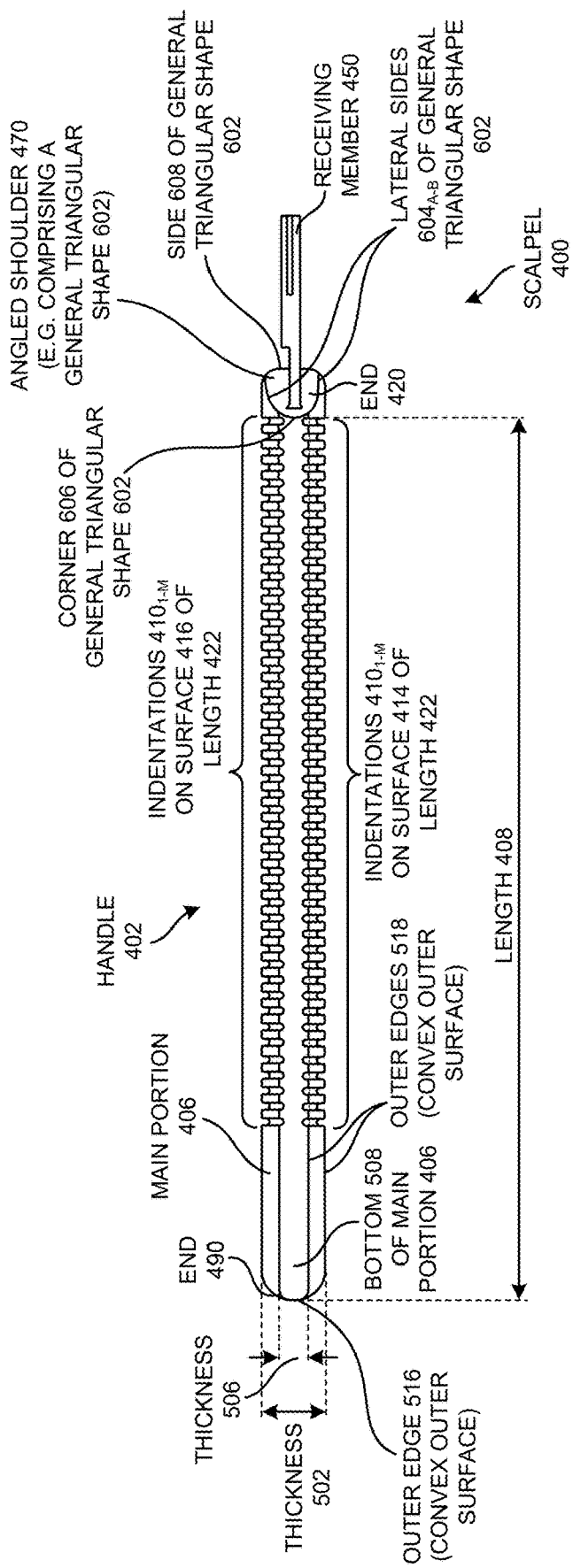
FIG. 6 is a bottom view of a handle of the scalpel of FIG. 4, according to one or more embodiments.
Figure 7:
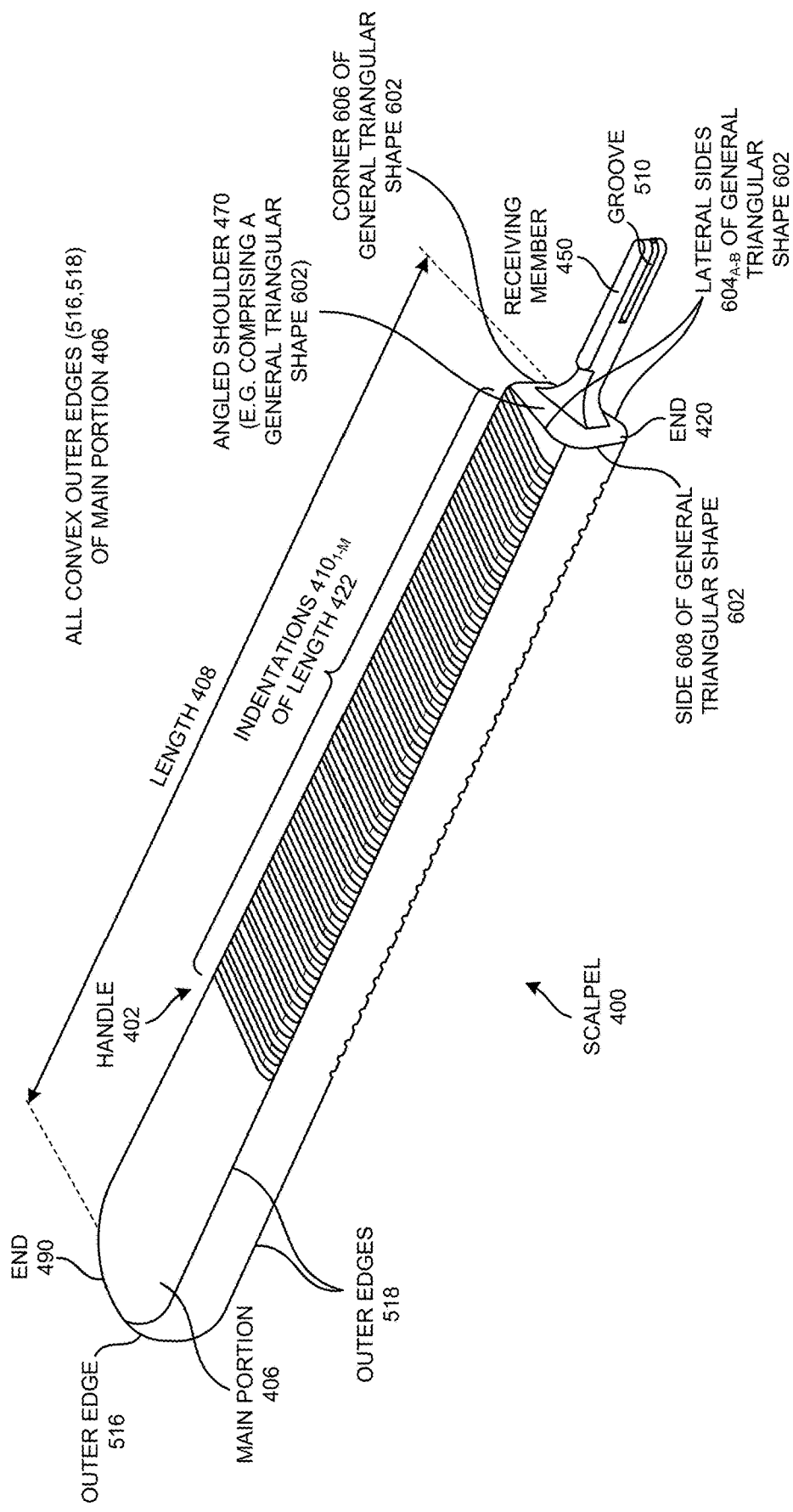
FIG. 7 is a perspective view of the handle of the scalpel of FIG. 4, according to one or more embodiments.

FIG. 6 shows a bottom view of handle 402 of scalpel 400 and FIG. 7 shows a perspective view of handle 402 of scalpel 400, according to one or more embodiments. As seen above, main portion 406 may enable increased comfort of user 250 during both a pen grip (analogous to pen grip 302) hold and a palm grip hold (analogous to palm grip 310) thereof at least because of the convex outer edges (516, 518), increased thickness (502, 506) and more length 422 of indentations 410$_{1-M}$ compared to analogues in main portion 106 of handle 102 of scalpel 100, according to one or more embodiments.

It should be noted that, although discussions associated with exemplary embodiments are directed toward convenience of user 250 with long hand 370 and/or fingers thereof, the relative dimensionalities of length 422 and length 408, width 412 and (maximum) width 480, and thickness (502, 506) and maximum thickness 514 render concepts discussed herein applicable to convenience of user 250 with any length of hand 370 and/or fingers thereof. All reasonable variations are within the scope of the exemplary embodiments discussed herein.

Although the present embodiments have been described with reference to specific example embodiments, it will be evident that various modifications and changes may be made to these embodiments without departing from the broader spirit and scope of the various embodiments. In addition, it will be appreciated that the various operations, processes, and methods disclosed herein may be performed in any order (e.g., including using means for achieving the various operations). Accordingly, the specification and drawings are to be regarded in an illustrative rather than a restrictive sense.

What is claimed is:

1. A scalpel handle comprising:
a receiving member comprising a groove along a length of the receiving member and a locking notch at a proximate end of the receiving member,
   wherein the groove is configured to receive a blade by sliding the blade through the groove, and
   wherein the locking notch at the proximate end of the receiving member to wrap around and lock onto the blade; and
a main portion coupled to the receiving member, the main portion having a plurality of indentations on both a first surface and a second surface thereof, each indentation of the plurality of indentations being evenly spaced from each adjacent indentation thereof and the plurality of indentations extending from a first end of the main portion proximate the receiving member and a projection of the first end on the main portion along a first length of the main portion across an entire width of the main portion, the projection of the first end being diametrically opposite to the first end along a first direction perpendicular to the first length of the main portion such that the first end and the projection of the first end delimit the width of the main portion in the first direction, the first length being greater than or equal to two-thirds of a second length of an entirety of the main portion but less than the second length, the width of the main portion being greater than or equal to five times a maximum width of the receiving member, and a thickness of the main portion being greater than or equal to 2.5 times a maximum thickness of the receiving member,
   wherein the length of the plurality of indentations extending from the first end of the main portion proximate to the receiving member is at least two-thirds of the length of the main portion,
wherein all outer surfaces of the main portion including the first surface and the second surface are convex in shape around edges thereof,
wherein the main portion comprises a second end farthest away from the receiving member and a third end closest to the receiving member, the third end also being proximate the first end and being free of any indentation of the plurality of indentations,
   wherein a thickness of the main portion at a top is more than a thickness at a bottom thereof to provide a surface to rest an index finger during use of the scalpel handle,
   wherein the top of the main portion is aligned with a spine of the blade and the bottom of the main portion is aligned with a cutting edge of the blade,
wherein the main portion further comprises an angled shoulder extending across the projection of the first end on the main portion and the third end such that the angled shoulder serves as a structural boundary of the main portion at the third end and the projection of the first end, the angled shoulder also being free of any indentation of the plurality of indentations therealong,
wherein the angled shoulder is generally triangularly shaped wherein the top of the main portion is generally a side of said general triangular shape, the first and second sides of the main portion are generally lateral sides of said general triangular shape, and the bottom of the main portion is generally where the two lateral sides of said general triangular shape meet to form a corner of said general triangular shape, and wherein the receiving member is external to the main portion and proximate the third end and the angled shoulder of the main portion along a second direction that is an extension of the first length of the main portion such that the receiving member along the second direction is within the width of the main portion projected outside the main portion.

2. The scalpel handle of claim 1, wherein the scalpel handle is made of one of: plastic and stainless steel.

3. The scalpel handle of claim 1, wherein the width of the main portion tapers from the second end thereof farthest away from the receiving member to the third end thereof closest to the receiving member, the width of the main portion at the third end still being greater than or equal to five times the maximum width of the receiving member.

4. The scalpel handle of claim 1, wherein:
the thickness of the main portion varies across the width thereof but is still always greater than or equal to 2.5 times the maximum thickness of the receiving member.

5. The scalpel handle of claim 1, wherein the receiving member one of: is coupled to the main portion and extends from the main portion.

6. A scalpel comprising:
a blade; and
a handle comprising:
  a receiving member receiving the blade therethrough; and
  a main portion coupled to the receiving member, the main portion having a plurality of indentations on both a first surface and a second surface thereof, each indentation of the plurality of indentations being evenly spaced from each adjacent indentation thereof and the plurality of indentations extending from a first end of the main portion proximate the receiving member and a projection of the first end on the main portion along a first length of the main portion across an entire width of the main portion, the projection of the first end being diametrically opposite to the first end along a first direction perpendicular to the first length of the main portion such that the first end and the projection of the first end delimit the width of the main portion in the first direction, the first length being greater than or equal to two-thirds of a second length of an entirety of the main portion but less than the second length, the width of the main portion being greater than or equal to five times a maximum width of the receiving member, and a thickness of the main portion being greater than or equal to 2.5 times a maximum thickness of the receiving member,
    wherein the length of the plurality of indentations extending from the first end of the main portion proximate to the receiving member is at least two-thirds of the length of the main portion,
    wherein all outer surfaces of the main portion including the first surface and the second surface are convex in shape around edges thereof,
    wherein the main portion comprises a second end farthest away from the receiving member and a third end closest to the receiving member, the third end also being proximate the first end and being free of any indentation of the plurality of indentations,
    wherein a thickness of the main portion at a top is more than a thickness at a bottom thereof to provide a surface to rest an index finger during use of the scalpel handle,
    wherein the top of the main portion is aligned with a spine of the blade and the bottom of the main portion is aligned with a cutting edge of the blade
    wherein the main portion further comprises an angled shoulder extending across the projection of the first end on the main portion and the third end such that the angled shoulder serves as a structural boundary of the main portion at the third end and the projection of the first end, the angled shoulder also being free of any indentation of the plurality of indentations therealong,
    wherein the angled shoulder is generally triangularly shaped wherein the top of the main portion is generally a side of said general triangular shape, the first and second sides of the main portion are generally lateral sides of said general triangular shape, and the bottom of the main portion is generally where the two lateral sides of said general triangular shape meet to form a corner of said general triangular shape, and
    wherein the receiving member is external to the main portion and proximate the third end and the angled shoulder of the main portion along a second direction that is an extension of the first length of the main portion such that the receiving member along the second direction is within the width of the main portion projected outside the main portion.

7. The scalpel of claim 6, wherein at least one of:
the handle is made of one of: plastic and stainless steel, and
the blade is made of stainless steel.

8. The scalpel of claim 6, wherein the width of the main portion of the handle tapers from the second end thereof farthest away from the receiving member to the third end thereof closest to the receiving member, the width of the main portion of the handle at the third end still being greater than or equal to five times the maximum width of the receiving member.

9. The scalpel of claim 6, wherein:
the thickness of the main portion of the handle varies across the width thereof but is still always greater than or equal to 2.5 times the maximum thickness of the receiving member.

10. The scalpel of claim 6, wherein the receiving member of the handle comprises:
a groove along a third length thereof through which the blade is slid.

11. The scalpel of claim 6, wherein the receiving member of the handle one of: is coupled to the main portion and extends from the main portion.

12. The scalpel of claim 6, wherein the receiving member of the handle comprises a locking notch proximate the third end to enable the receiving member wrap around and lock onto the blade.

13. A scalpel handle comprising:
a receiving member configured to receive a blade; and
a main portion coupled to the receiving member, the main portion having a plurality of indentations on both a first surface and a second surface thereof, each indentation of the plurality of indentations being evenly spaced from each adjacent indentation thereof and the plurality of indentations extending from a first end proximate the receiving member and a projection of the first end on the main portion along a first length of the main portion across an entire width of the main portion, the projection of the first end being diametrically opposite to the first end along a first direction perpendicular to the first length of the main portion such that the first end and the projection of the first end delimit the width of the main portion in the first direction, the first length being greater than or equal to two-thirds of a second length of an entirety of the main portion but less than the second length, the width of the main portion being greater than or equal to five times a maximum width of the receiving member, and a thickness of the main portion being greater than or equal to 2.5 times a maximum thickness of the receiving member,
- wherein the length of the plurality of indentations extending from the first end of the main portion proximate to the receiving member is at least two-thirds of the length of the main portion, wherein all outer surfaces of the main portion including the first surface and the second surface are convex in shape around edges thereof, wherein the main portion comprises a second end farthest away from the receiving member and a third end closest to the receiving member, the third end also being proximate the first end and being free of any indentation of the plurality of indentations,
- wherein a thickness of the main portion at a top is more than a thickness at a bottom thereof to provide a surface to rest an index finger during use of the scalpel handle,
- wherein the top of the main portion is aligned with a spine of the blade and the bottom of the main portion is aligned with a cutting edge of the blade, wherein the main portion further comprises an angled shoulder extending across the projection of the first end on the main portion and the third end such that the angled shoulder serves as a structural boundary of the main portion at the third end and the projection of the first end, the angled shoulder also being free of any indentation of the plurality of indentations therealong,
- wherein the angled shoulder is generally triangularly shaped wherein the top of the main portion is generally a side of said general triangular shape, the first and second sides of the main portion are generally lateral sides of said general triangular shape, and the bottom of the main portion is generally where the two lateral sides of said general triangular shape meet to form a corner of said general triangular shape, wherein the width of the main portion tapers from the second end thereof farthest away from the receiving member to the third end thereof closest to the receiving member, the width of the main portion at the third end still being greater than or equal to five times the maximum width of the receiving member, and wherein the receiving member is external to the main portion and proximate the third end and the angled shoulder of the main portion along a second direction that is an extension of the first length of the main portion such that the receiving member along the second direction is within the width of the main portion projected outside the main portion.

14. The scalpel handle of claim 13, wherein the scalpel handle is made of one of:
plastic and stainless steel.

15. The scalpel handle of claim 13, wherein:
the thickness of the main portion varies across the width thereof but is still always greater than or equal to 2.5 times the maximum thickness of the receiving member.

16. The scalpel handle of claim 13, wherein the receiving member comprises:
a groove along a third length thereof.

17. The scalpel handle of claim 13, wherein the receiving member one of: is coupled to the main portion and extends from the main portion.

18. The scalpel handle of claim 13, wherein the receiving member comprises a locking notch proximate the third end.

* * * * *